United States Patent
Tewari et al.

(10) Patent No.: US 10,172,944 B2
(45) Date of Patent: Jan. 8, 2019

(54) COPROCESSED SILICA COATED POLYMER COMPOSITION

(71) Applicant: HERCULES INCORPORATED, Wilmington, DE (US)

(72) Inventors: Divya Tewari, West Chester, PA (US); Yevgeniya A. Titova, Wilmington, DE (US); Brad Beissner, Wilmington, DE (US); Thomas Durig, Chadds Ford, PA (US)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 14/764,306

(22) PCT Filed: Mar. 12, 2014

(86) PCT No.: PCT/US2014/024934
§ 371 (c)(1),
(2) Date: Jul. 29, 2015

(87) PCT Pub. No.: WO2014/165241
PCT Pub. Date: Oct. 9, 2014

(65) Prior Publication Data
US 2016/0120989 A1    May 5, 2016

Related U.S. Application Data

(60) Provisional application No. 61/777,604, filed on Mar. 12, 2013.

(51) Int. Cl.

| | |
|---|---|
| *A61K 47/32* | (2006.01) |
| *A61K 9/20* | (2006.01) |
| *A61K 47/38* | (2006.01) |
| *A61K 31/522* | (2006.01) |
| *A61J 3/10* | (2006.01) |
| *A61K 47/02* | (2006.01) |
| *C09D 139/06* | (2006.01) |
| *C09J 139/06* | (2006.01) |

(52) U.S. Cl.
CPC ............ *A61K 47/32* (2013.01); *A61J 3/10* (2013.01); *A61K 9/2009* (2013.01); *A61K 9/2027* (2013.01); *A61K 9/2054* (2013.01); *A61K 31/522* (2013.01); *A61K 47/02* (2013.01); *A61K 47/38* (2013.01); *C09D 139/06* (2013.01); *C09J 139/06* (2013.01)

(58) Field of Classification Search
CPC   A61J 3/10; A61K 47/02; A61K 47/38; A61K 9/2054; C09D 139/06; C09J 139/06
See application file for complete search history.

(56) References Cited

U.S. PATENT DOCUMENTS

| | | | | |
|---|---|---|---|---|
| 5,211,958 A | * | 5/1993 | Akkerboom | A61K 9/2054 424/465 |
| 6,471,994 B1 | * | 10/2002 | Staniforth | A61K 9/2009 264/112 |
| 2001/0001664 A1 | * | 5/2001 | Sherwood | A61K 9/2009 424/400 |
| 2008/0213360 A1 | | 9/2008 | Thoorens et al. | |
| 2010/0285164 A1 | * | 11/2010 | Schaible | A61K 9/0056 424/777 |
| 2011/0151014 A1 | | 6/2011 | Thoorens et al. | |
| 2011/0133956 A1 | | 10/2011 | Van Goor et al. | |

OTHER PUBLICATIONS

US Pharmacopeia (Hydroxypropyl cellulose, available on-line on Jun. 28, 2011, found on Wayback Machine and downloaded in Nov. 2017).*
Wayback Machine (Dates of availability for the US Pharmacopeia reference to hydroxypropyl cellulose, downloaded in Nov. 2017).*
International Search Report, PCT/US2014/024934 published on Jul. 7, 2014.

* cited by examiner

*Primary Examiner* — Mark V Stevens
(74) *Attorney, Agent, or Firm* — Thompson Hine LLP; William J. Davis

(57) ABSTRACT

An excipient composition having good bulk density and improved flow characteristics is provided. The present invention particularly provides a coprocessed excipient composition and a method of producing the same. The coprocessed excipient comprises cellulose derived polymer and a deagglomerated coprocessing agent. The coprocessing agent is fumed silica, colloidal silica or silicon dioxide. The coprocessed excipient is prepared in a continuous process and has excellent compactability and improved flow property as measured by Johanson flow rate number increase from 1.1 to 5.0 fold, is characterized by a Brookfield cohesion factor of less than 0.2 kPa and a bulk density of at least 0.249 g/ml.

13 Claims, 8 Drawing Sheets

1) Milling Feed
2) Rotor
3) Impact Beater
4) Milling Gap
5) Stator
6) Outlet Gap
7) Alternative Stator (Screen) with Outlet Through the Screen Perforation

Gravitational force
Promotes flow
increases with higher density

Inter-particle cohesion counteracts flow
Increases with smaller particle size, surface roughness, particle irregularity, moisture and charge

COPROCESSED SILICA COATED POLYMER COMPOSITION

FIELD OF THE INVENTION

The present invention relates to a coprocessed excipient composition and to a method of producing the same. The present invention particularly relates to a coprocessed excipient comprising cellulose derived polymer and a deagglomerated coprocessing agent.

BACKGROUND OF THE INVENTION

Excipient powders frequently exhibit poor flow and compaction behavior. Various techniques such as wet granulation, spray drying, mechanofusion, and grinding have been employed to improve the flow and compaction behavior.

Cellulose derivatives are important polysaccharide derivatives. These are widely used in various industrial applications, for example, in personal care, pharmaceutical, agricultural construction and energy. One of the important applications of the cellulose polymers, particularly water-soluble cellulose derivatives, is their incorporation as excipients in sustained release dosage forms. Sustained release dosage forms are designed to release a drug at a predetermined rate in order to maintain a constant drug concentration for a specific period of time with minimum side effects. This can be achieved through a variety of formulations, including polymer matrix in dosage forms. Sustained release pharmaceutical dosage forms maintain therapeutic serum levels of medicaments and minimize the effects of missed doses of drugs caused due to lack of patient compliance.

U.S. Pat. No. 4,734,285 assigned to Dow Chemical Company discloses delayed release solid tablets of a therapeutically active composition and a process to prepare such a composition. Fine particles, which can pass a 100 mesh screen (149 micrometer mesh size) and preferably 140 mesh screen (105 micrometer mesh size), of hydroxypropyl methylcellulose ether composition are present as an excipient in the solid tablet. These fine particles are very small in size and show poor flow properties. Poor particle flow can lead to consolidation of the powder bed in processing equipment, such as storage bins and tablet press feed hoppers. Problems can include increased inconsistency in tablet weight or tablet crushing strength from tablet-to-tablet as well as inconsistency in the amount of active ingredient incorporated into each dosage form.

WO2004/022601 assigned to JRS Pharma LP and U.S. Pat. No. 5,585,115 assigned to Edward H. Mendell Co., Inc. disclose an agglomerated microcrystalline cellulose blend containing silicon dioxide, purported to have improved compressibility. The disclosure states that silicon dioxide is a critical component to improve compressibility. The two step process described includes spray granulation followed by wet granulation. The prepared granules in this process are further dried using heat, which is not advantageous. However, granulation is time consuming and adds cost to the process due to the time lost, additional labor, energy consumption and additional equipment required.

Several processes for drying-grinding moist cellulose derivatives are known in the art, such as described in the patent applications GB 2262527A; EP 0 824 107 A2; EP-B 0 370 447 (equivalent to U.S. Pat. No. 4,979,681); EP 1 127 895 A1 (equivalent to U.S. Pat. No. 6,509,461); EP 0 954 536 A1 (equivalent to U.S. Pat. No. 6,320,043); WO96/00748 A1; WO2011/046679 (equivalent to US 2012/187225) and WO2012/138532.

US2012/160944A1 assigned to ICEUTICA PTY LTD discloses a method to produce nano and micro-particle powders of a biologically active material which have improved powder handling properties using dry milling process.

WO2012/116402A1 assigned to University of Monash discloses binder powders for use in powder material processing and processes for their preparation by using techniques such as spray drying and mechanofusion. These processes lead to reduction in particle size of the polymer. Moreover, these processes are costly and time consuming.

The increase in flow of cellulose polymers by co-milling microcrystalline cellulose with nano-silica is described in J. Pharm. Sci. 2011 November; 100(11):4943-52, Chattoraj S, Shi L, Sun CC.

Moreover, spray drying, mechanofusion, magnetic assisted impaction, hybridizer and grinding require specialized instruments that are commonly not available at manufacturing units.

Surprisingly, it has been found that bulk density and flowability of cellulose derived polymer can be increased by a novel continuous process comprising coprocessing the polymer and a coprocessing agent using high shear.

Thus, the present invention relates to a coprocessed excipient composition comprising cellulose derived polymer and a deagglomerated coprocessing agent. The coprocessed excipient is prepared in a continuous process and has excellent compactability and improved flow property as measured by Johanson flow rate number increased from 1.1 to 5.0 fold, is characterized by a Brookfield cohesion less than 0.20 kPa, a bulk density of at least 0.249 g/ml. The coprocessing agent is fumed silica, colloidal silica, silicon dioxide or a combination thereof.

SUMMARY OF THE INVENTION

The present invention provides a coprocessed excipient comprising cellulose derived polymer and a deagglomerated coprocessing agent. The coprocessed excipient is prepared in a continuous process and has a Brookfield cohesion of less than 0.20 kPa and a bulk density of at least 0.249 gram/milliliter and a flow property as measured by Johanson flow rate number increased from 1.1 to 5.0 fold The cellulose derived polymer used in the present invention is selected from the group comprising ethyl cellulose, hydroxyethyl cellulose (HEC), hydroxypropyl cellulose (HPC), ethyl hydroxyethyl cellulose (EHEC), carboxymethyl hydroxyethyl cellulose (CMHEC), hydroxypropyl hydroxyethyl cellulose (HPHEC), methyl cellulose (MC), methyl hydroxypropyl cellulose (MHPC), methyl hydroxyethyl cellulose (MHEC), carboxymethyl cellulose (CMC), hydrophobically modified hydroxyethyl cellulose (hmHEC), hydrophobically modified hydroxypropyl cellulose (hmHPC), hydrophobically modified ethyl hydroxyethyl cellulose (hmEHEC), hydrophobically modified carboxymethyl hydroxyethyl cellulose (hmCMHEC), hydrophobically modified hydroxypropyl hydroxyethyl cellulose (hmHPHEC), hydrophobically modified methyl cellulose (hmMC), hydrophobically modified methyl hydroxypropyl cellulose (hmMHPC), hydrophobically modified methyl hydroxyethyl cellulose (hmMHEC), hydrophobically modified carboxymethyl methyl cellulose (hmCMMC), sulfoethyl cellulose (SEC), hydroxyethyl sulfoethyl cellulose (HESEC), hydroxypropyl sulfoethyl cellulose (HPSEC), methyl hydroxyethyl sulfoethylcellulose (MHESEC), methyl hydroxypropyl sulfoethyl cellulose (MHPSEC), hydroxyethyl hydroxypropyl sulfoethyl cellulose (HEHPSEC), carboxymethyl sulfoethyl cellulose (CM-SEC), hydrophobically modified sulfoethyl cellulose (hm-SEC), hydrophobically modified hydroxyethyl sulfoethyl cellulose (hmHESEC), hydrophobically modified hydroxypropyl sulfoethyl cellulose (hmHPSEC) and hydrophobically modified hydroxyethyl hydroxypropyl sulfoethyl cellulose (hmHEHPSEC) and/or combinations thereof.

In a preferred embodiment the cellulose derived polymer is selected from ethyl cellulose, methylcellulose, methyl ethyl cellulose, hydroxyethyl cellulose, hydroxypropyl cellulose, hydroxyethylmethyl cellulose, hydroxypropyl methylcellulose, and carboxymethyl cellulose.

In a particular embodiment the coprocessing agent is selected from fumed silica, colloidal silica, silicon dioxide, calcium silicate or a combination thereof.

The cellulose derived polymer is present in an amount of about 90.0% to about 99.9% and coprocessing agent is present in an amount of about 0.1% w/w to about 10.0% w/w of the total coprocessed excipient composition.

In one particular embodiment, the weight ratio of cellulose derived polymer to coprocessing agent is about 90:10, 95:5, 98:2, 99:1 or even 99.9 to 0.1.

The coprocessed excipient of the present invention is further combined with an active or functional ingredient selected from paints and coatings, personal care, detergents, pharmaceuticals, neutraceuticals, ceramics, insulators, pet food, animal food and human food, agricultural products, adhesives, electroplating, inks, dyes, paper, catalytic convertors and electronics.

Yet another aspect of the present invention provides a process to prepare coprocessed excipient comprising the steps of:
  i. deagglomerating a coprocessing agent using shear in magnitude of at least 0.01 kW-hr/kg;
  ii. passing a cellulose derived polymer and deagglomerated coprocessing agent through a blender with an average particle residence time of >1 second;
  iii. subjecting the above two components to pass through a universal mill;
  iv. maintaining an average particle residence time within the universal mill system to be >1 seconds completed by a continuous recycle process; and
  v. obtaining the coprocessed excipient having a Brookfield Cohesion of at least less than 0.2 kPa, a bulk density of at least 0.249 gram/milliliter and a flow property as measured by Johanson flow rate number increase from 1.1 to 5.0 fold.

In a preferred embodiment, the universal mill consists of a rotor with tip speed for about 15 meters/second to about 150 meters/second and screen size of about 0.2 millimeter to about 0.9 millimeter.

Yet another aspect of the present invention discloses a composition comprising coprocessed excipient of a cellulose derived polymer and a deagglomerated coprocessing agent. The composition is used in various industrial applications selected from paints and coatings, personal care, detergents, pharmaceuticals, neutraceuticals, ceramics, insulators, pet food, animal food and human food, agricultural products, adhesives, electroplating, inks, dyes, paper, catalytic convertors and electronics.

In a preferred embodiment the composition is used in pharmaceuticals.

In a preferred embodiment the composition is formulated into an oral dosage form such as a tablet, by dry granulation, direct compression or hot melt extrusion processing.

The present invention provides a directly compressible pharmaceutical composition comprising an active pharmaceutical ingredient and coprocessed excipient.

Yet another aspect of the present invention provides a direct compression process comprising the steps of
i) blending an active pharmaceutical ingredient, the coprocessed excipient, and optionally one more pharmaceutically acceptable adjuvants to produce a blend with improved flow property and
ii) compressing the resulting composition to get the product with improved drug content uniformity and improved capacity.

In a preferred embodiment the directly compressible pharmaceutical composition is formulated into modified release, controlled release, sustained release, immediate release, extended release dosage forms or soluble dosage form.

The present invention provides a process to prepare a directly compressible pharmaceutical composition comprising blending the active pharmaceutical ingredient, the coprocessed above-described, and optionally one or more adjuvants and compressing the resulting components to obtain directly compressible pharmaceutical composition.

DETAILED DESCRIPTION OF THE INVENTION

Figure 7A:
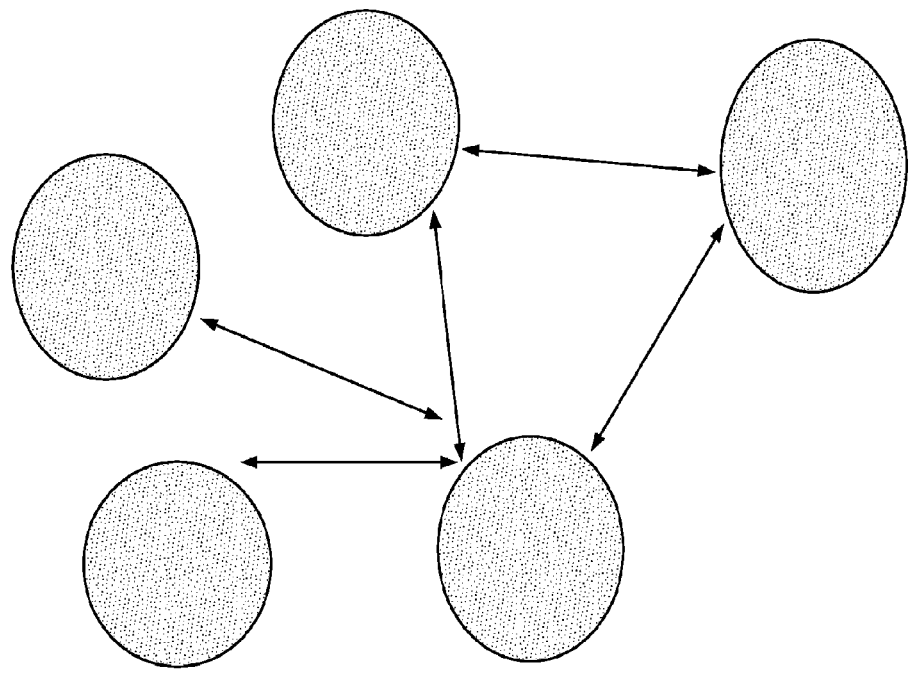
FIGS. 7 (A & B) represents enhanced flow as a result of low Interparticle Brookfield Cohesion.
Figure 7B:
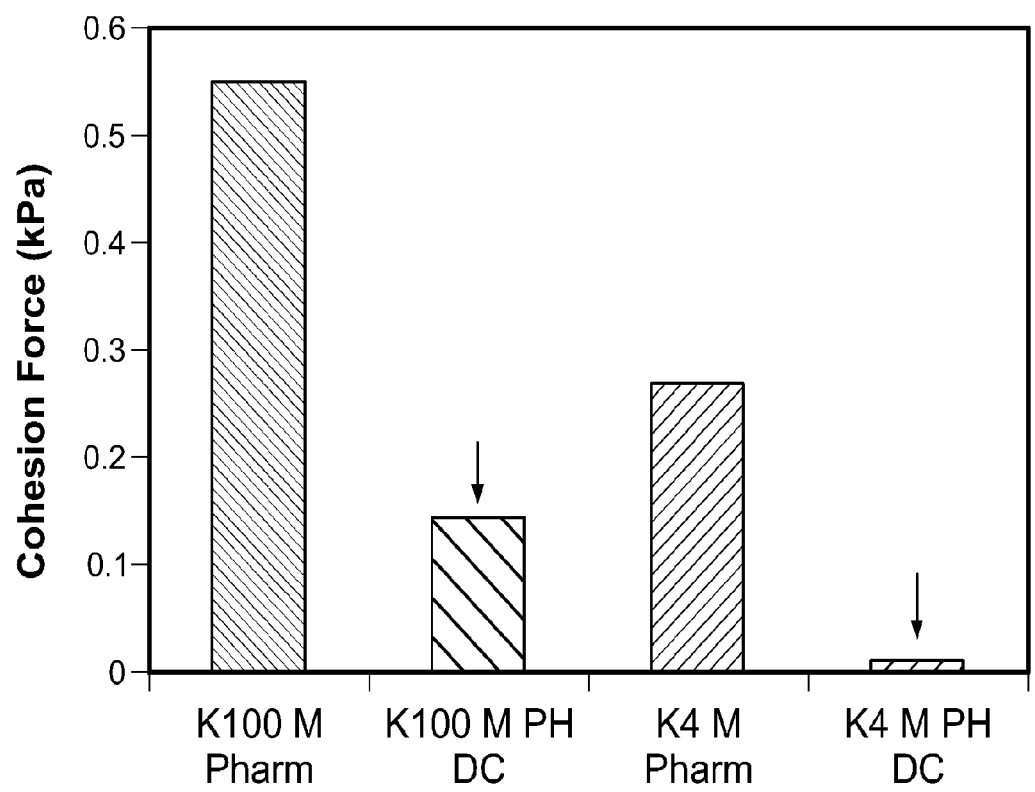

Typical polymers used for the direct compression formulations have a fibrous nature, small particle size, strong inter-particle cohesion and surface charge, which lead to a poor flow in pharmaceutical unit process. Formulators often have to use a granulation step to overcome these challenges to powder flow. The powder flow is affected by gravitational forces (influenced by bulk density) and the interparticle cohesion and a balance is needed between the two to improve the flow (as shown in FIG. 7). Not to be bound by any theories, the inventors of the present invention discovered that increased flowability is observed when an additive is coprocessed with the polymeric powder whose flowability is to be increased. Enhanced flow rate of almost 5 fold was unexpectedly achieved as a result of very low interparticle cohesion and higher bulk density.

There are several advantages for using the coprocessed excipient of the present invention: (i) reduced processing time and production costs, no additional capital investment is necessary for adopting this flow-improvement technique; (ii) improved powder flow; (iii) improved content uniformity (iv) dissolution profiles comparable with other commercial polymeric grade available in the market; (v) the present process is fast, continuous, and scalable. Hence, it can be readily adopted during both development and manufacturing of pharmaceutical products.

Throughout this specification and the claims which follow, unless the context requires otherwise, the word "comprise" and variations such as "comprises" and "comprising", will be understood to imply the inclusion of a stated integer or step or group or integers or steps but not the exclusion of any other integer or step or group or integers or steps.

The singular forms "a", "an" and "the" include plural aspects unless the context clearly dictates otherwise.

All aspects, embodiments and examples described herein are encompassed by the term "invention".

As used herein, the term "m/sec" refers to the units of rotor speed in meters per second.

As used herein, the term "mm" refers to the units of mesh size in millimeters.

As used herein, the term "bulk density" refers to Bulk density (BD is defined as the ratio of apparent volume to mass of the material taken, called untapped bulk density, and also the ratio of tapped volume to mass of material taken, called tapped bulk density. A useful procedure for measuring these bulk densities is described in United States Pharmacopeia 24, Test 616 "Bulk Density and Tapped Density," United States Pharmacopeia Convention, Inc., Rockville, Md., 1999.

As used herein, the term "Flow Rate Indicizer" refers to an instrument manufactured by Johnson, that was used to characterize properties such as FRI (flow rate index), FDI (Flow density index), BDI (Bin density index), and SBI (Spring back index).

As used herein, the term "Johanson flow rate number" refers to Flow Rate Index (FRI), which is a measure of a powder's limiting flow rate through a container after deaeration. The negative direction for the FRI is a decrease. The FRI is also useful for correlating particle sizes and size distribution if the mean particle size remains constant. A lower FRI indicates a smaller particle size or a wider size distribution if the mean size remains unchanged.

As used herein, the term "deagglomeration" refers to a process of breaking up or dispersing that which has agglomerated, aggregated, or clustered together.

The term "coprocessed excipient composition" as used herein, refers to a coprocessed excipient that is a combination of two or more compendial or non-compendial excipients designed to physically modify their properties in a manner not achievable by simple physical mixing and without significant chemical change.

As used herein, the term "Universal Mill" refers to a high speed fine impact mill for the dry grinding or deagglomerating of various products. In particular the mill is utilized as a rotor impact mill, which is characterized by an impact process between the rotor and a stator (such as a screen). Material and air enter the mill and are subject to centrifugal forces from the rotor; subsequently the impact beater forces the material through the milling gap provided by the stator (grinding track and screen). Various configurations of the rotor/impact beater include the wing beater and blast rotor.

As used herein, the term "Blender" refers to a continuous single or double helix ribbon blender with a residence time of at least one second; or a blender with similar capability that allows for mixing in a continuous process, a residence time of at least one second, and shaft speed of 10-30 rotations per minute.

The term "Brookfield Cohesion" as used herein, refers to a failure strength measured at an applied compression force in time consolidation test of Brookfield powder flow tester (ASTM D6128). In preferred embodiments, the Brookfield Cohesion is less than 0.20 kPa. Preferably less than 0.15 kPa, and more preferably less than 0.10 kPa.

The term "compaction" as used herein, refers to a simultaneous process of compression and consolidation of a two phase system (solid-air) due to the applied force.

As used herein, the term "Direct compression" or "DC" refers to obtaining a formulation by directly compressing and molding a raw material powder. This process is described in publications such as The Theory and Practice of Industrial Pharmacy (Third Edition) (Leon Lachman, et al.: LEA & FEBIGER 1986) and Pharmaceutical Dosage Forms: Tablets Volume 1 (Second Edition) (Herbert A. Lieberman, et al.: MARCEL DEKKER INC. 1989).

As used herein, the term "continuous process" refers to production that is not executed batch wise but steadily, such as production on a continuous blend. In non-continuous processes, i.e., batch production processes, insertion of the raw materials into the machine/mill and subsequent unloading of the newly produced composition from the machine/mill occupies too much time to make low-cost production possible. The significance of the term "continuous production" here is the implication of the advantages gained by an assembly line with each step characterized by an average residence time.

The present invention provides a coprocessed excipient comprising a cellulose derived polymer and a deagglomerated coprocessing agent.

The coprocessed excipient is prepared in a continuous process and has a Brookfield cohesion of less than 0.2 kPa, a bulk density of at least 0.249 gram/milliliter and a flow property as measured by Johanson flow rate number increased from 1.1 to 5.0 fold. The coprocessing agent is fumed silica, colloidal silica, silicon dioxide or a combination.

Cellulose derived polymers useful in the practice of the present invention can be selected from the group comprising ethyl cellulose, hydroxyethyl cellulose (HEC), hydroxypropyl cellulose (HPC), ethyl hydroxyethyl cellulose (EHEC), carboxymethyl hydroxyethyl cellulose (CMHEC), hydroxypropyl hydroxyethyl cellulose (HPHEC), methyl cellulose (MC), methyl hydroxypropyl cellulose (MHPC), methyl hydroxyethyl cellulose (MHEC), carboxymethyl cellulose (CMC), hydrophobically modified hydroxyethyl cellulose (hmHEC), hydrophobically modified hydroxypropyl cellulose (hmHPC), hydrophobically modified ethyl hydroxyethyl cellulose (hmEHEC), hydrophobically modified carboxymethyl hydroxyethyl cellulose (hmCMHEC), hydrophobically modified hydroxypropyl hydroxyethyl cellulose (hmHPHEC), hydrophobically modified methyl cellulose (hmMC), hydrophobically modified methyl hydroxypropyl cellulose (hmMHPC), hydrophobically modified methyl hydroxyethyl cellulose (hmMHEC), hydrophobically modified carboxymethyl methyl cellulose (hmCMMC), sulfoethyl cellulose (SEC), hydroxyethyl sulfoethyl cellulose (HESEC), hydroxypropyl sulfoethyl cellulose (HPSEC), methyl hydroxyethyl sulfoethylcellulose (MHESEC), methyl hydroxypropyl sulfoethyl cellulose (MHPSEC), hydroxyethyl hydroxypropyl sulfoethyl cellulose (HEHPSEC), carboxymethyl sulfoethyl cellulose (CM-SEC), hydrophobically modified sulfoethyl cellulose (hm-SEC), hydrophobically modified hydroxyethyl sulfoethyl cellulose (hmHESEC), hydrophobically modified hydroxypropyl sulfoethyl cellulose (hmHPSEC) and hydrophobically modified hydroxyethyl hydroxypropyl sulfoethyl cellulose (hmHEHPSEC) and/or combinations thereof.

Most preferably, the cellulose derived polymer can be selected from the group comprising methylcellulose, ethyl cellulose, methyl ethyl cellulose, hydroxyethyl cellulose, hydroxypropyl cellulose, hydroxyethylmethyl cellulose, hydroxypropyl methylcellulose, and carboxymethyl cellulose.

The term "Hydroxypropylcellulose (HPC)" as used herein, including the claims, refers to a water soluble polymer available in different pharmaceutical grades. A particularly preferred source of HPC is Ashland Specialty Ingredients (Wilmington, Del.), which markets HPC under the trade name of KLUCEL™.

The term "Hydroxypropyl methyl cellulose (HPMC)" as used herein, including the claims, A particularly preferred source of HPMC is Ashland Specialty Ingredients (Wilmington, Del.), which markets HPMC under the trade name of BENECEL™.

The term "Hydroxyethyl cellulose (HEC)" as used herein, including the claims, refers to a polymer available in different pharmaceutical grades. A particularly preferred source of HEC is Ashland Specialty Ingredients (Wilmington, Del.), which markets HEC under the trade name of Natrosol™.

The term "Carboxymethyl cellulose (CMC) sodium" as used herein is particularly preferred source of CMC is Ashland Specialty Ingredients (Wilmington, Del.), which markets CMC under the trade names Aqualon® or Blanose™.

Particularly, silica of the present invention is selected from the group comprising fumed silica, colloidal silica, silicon dioxide, calcium silicate and/or a combination thereof.

Silica useful in the practice of the present invention is silicon dioxide, particularly colloidal silicon dioxide that has particles size particularly less than 500 nm, more particularly less than 400 nm Those skilled in the art will appreciate that the name and/or method of preparation of the silicon dioxide utilized in the present invention is not determinative of the usefulness of the product. Rather, it has been surprisingly discovered that it is the physical characteristics of the silicon dioxide which are critical. In particular, it has been discovered that silicon dioxide having a relatively large particle size (and correspondingly small surface area), such as silica gel, is not useful in the current invention. Silica itself is a submicron, fluffy, light, loose, bluish-white, odorless and tasteless amorphous powder which is commercially available from a number of sources, including Cabot Corporation (under the tradename Cab-O-Sil); Degussa, Inc. (under the tradename Aerosil); E.I. DuPont & Co.; and W.R. Grace & Co. Colloidal silicon dioxide is also known as colloidal silica, fumed silica, amorphous fumed silica, silicon dioxide, amorphous silica, light anhydrous silicic acid, silicic anhydride, and silicon dioxide fumed, among others. However, the amount of silicon dioxide included in pharmaceutical applications is limited and it is in the range of 0.01-1% by weight. Handbook of Pharmaceutical Excipients, COPYRGT. 1986 American Pharmaceutical Association, page 255.

In further embodiments, the cellulose derived polymer is present in an amount of about 90.0% to about 99.9% and coprocessing agent is present in an amount of about 0.1% w/w to about 10.0% w/w of the total coprocessed excipient composition.

In one particular embodiment, the weight ratio of cellulose derived polymer to coprocessing agent is about 90:10, 95:5, 98:2, 99:1 or even 99.9 to 0.1. Alternatively, the amount coprocessing agent may be expressed as wt/wt %, of cellulose derived polymer or the lactam derived polymer, for example, 0.1%, 0.25%, 0.5%, 0.75%, 1.0%, 2.5%, 5%, or 10%.

The present coprocessed excipient can be further combined with an active or functional ingredient selected from paints and coatings, personal care, detergents, pharmaceuticals, neutraceuticals, ceramics, insulators, pet food, animal food and human food, agricultural products, adhesives, electroplating, inks, dyes, paper, catalytic convertors and electronics.

The present invention provides a continuous process to prepare coprocessed excipient comprising the steps of:
  i. deagglomerating a coprocessing agent using shear in magnitude of at least 0.01 kW-hr/kg;
  ii. passing a cellulose derived polymer and deagglomerated coprocessing agent through a blender with an average particle residence time of >1 second;
  iii. subjecting the above two components to pass through a universal mill;
  iv. maintaining an average particle residence time within the universal mill system to be >1 seconds completed by a continuous recycle process; and
  v. obtaining the coprocessed excipient having a Brookfield Cohesion of less than 0.20 kPa, a bulk density of at least 0.249 gram/milliliter and a flow property as measured by Johanson flow rate number increased from 1.1 to 5.0 fold.

In further embodiments, the universal mill consists of a rotor with tip speed for about 15 meters/second to about 150 meters/second and screen size of about 0.2 millimeter to about 0.9 millimeter The present invention provides a direct compressible pharmaceutical composition comprising an active pharmaceutical ingredient, which is not more than 1.0% of the coprocessed excipient and optionally one or more pharmaceutically acceptable additives. The direct compression process comprises the steps of
  i. blending the active pharmaceutical ingredient, the coprocessed excipient having a Brookfield cohesion of less than 0.20 kPa, a bulk density of at least 0.249 gram/milliliter and improved flow property as measured by Johanson flow rate from about 1.1 to about 5.0 fold, and optionally one or more adjuvants without adding a substantial amount of added solvent or heat; and
  ii. compressing the resulting components to obtain directly compressible pharmaceutical composition.

The present invention provides a direct compressible pharmaceutical composition comprising an active pharmaceutical ingredient, the above-described coprocessed excipient and optionally one or more pharmaceutically acceptable additives.

The present invention provides a direct compression process comprising the steps of
i. blending the active pharmaceutical ingredient, the coprocessed excipient having a Brookfield cohesion of less than 0.20 kPa, a bulk density of at least 0.249 gram/milliliter and a flow property as measured by Johanson flow rate number increase from 1.1 to 5.0 fold, and optionally one or more adjuvants without adding a substantial amount of added solvent or heat; and
ii. compressing the resulting components to obtain directly compressible pharmaceutical composition.

Figure 6:
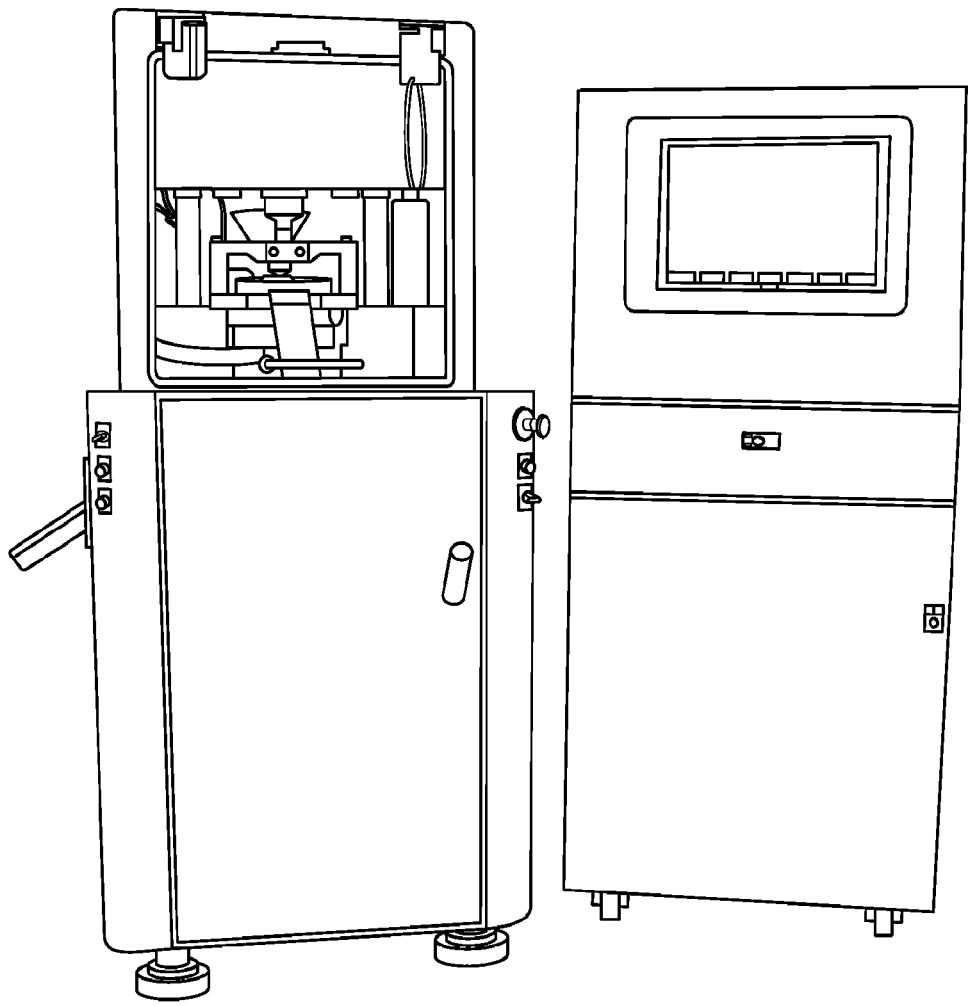
FIG. 6 represents a diagram of a STYLCAM 200R, a single-punch rotary tablet press.

In one of the preferred embodiment, STYLCAM 200R Simulator (from Mendel Pharma), (as shown in FIG. 6) a single punch rotary tablet press is used to duplicate and analyze precompression, compression, and ejection phases in industrial tablet-production presses under identical conditions to those of a unit producing up to 300,000 tablets per hour. Equipped with a computer interface and data acquisition software, it enables users to select different compression profiles to simulate different types of rotary tableting presses. It enables the formulator to understand the scalability and compressibility of the formulation blend before going to large batches of material. Pure polymer compaction (99% polymer and 1% Cab-O-Sil) studies were conducted using Stylcam 200R compaction simulator using 11.28 mm flat round Euro D tooling.

The following examples further illustrate the invention.

Example 1: Coprocessing of Hydroxypropyl Methyl Cellulose (HPMC) and Deagglomerated Silica The coprocessing performed by co-milling powdered hydroxypropyl methyl cellulose (Grade: HPMC K100M) with silica. The silica-coating of the hydroxypropyl methyl cellulose (HPMC) was accomplished by geometric dilution of the powdered polymer with silica by sieving and then passing through a blender and then through a universal mill, which is fitted with a blunt impeller. The steps include deagglomeration of silica powder and subsequently at least with a partial coating of silica on the powdered polymer. The speed of the impeller was 3000 rpm and screen size was 0.5 mm and mesh size is 35 with 0.0075 inches during the process. Bulk density of the resulted samples was measured and listed in Table 1.

TABLE 1

Bulk density of invention samples (Silica coated HPMC K100M) and control samples

| | Weight of 60 mL (g) | No. of Avalanches | Mean time to avalanche (s) | Avalanche scatter (s) | Max Time to Avalanche (s) | Bulk Density (g/mL) |
|---|---|---|---|---|---|---|
| Control 1: Dow DC HPMC 100M | 9.94 | 100 | 5.28 | 2.86 | 13.00 | 0.166 |
| Control 2: Benecel K100 | 17.44 | 107 | 4.97 | 3.22 | 12.33 | 0.291 |
| Control 3: Benecel K100M | 17.21 | 116.33 | 4.52 | 2.93 | 11.00 | 0.287 |
| Invention 1: Benecel K100M coated with SiO$_2$ (DC) | 17.88 | 139 | 3.80 | 2.41 | 16.0 | 0.298 |

Example 2: Coprocessing of Hydroxypropyl Methyl Cellulose (HPMC) and Silica

The same process described in Example 1 was repeated with hydroxypropyl methyl cellulose (HPMC) of grade HPMC K4M by replacing the mesh size to 50.

Example 3: Coprocessing of Hydroxyethyl Cellulose (HEC) and Silica

The same process described in Example 1 was repeated with hydroxy cellulose and silica.

Example 4: Coprocessing of Carboxymethyl Cellulose (CMC) and Silica

The same process described in Example 1 was repeated with Carboxymethyl cellulose (CMC) and silica.

Example 6: Coprocessing of Hydroxypropyl Cellulose (HPC) and Silica

The same process described in Example 1 was repeated hydroxypropyl cellulose (HPC) and silica by changing impeller speed to 2000 rpm and replacing the mesh size to 50. Bulk densities of the resulted samples were measured and listed in Table 2.

TABLE 2

Bulk density of invention samples (Silica coated HPC) and control samples

| | Weight of 60 mL (g) | No. of Avalanches | Mean Time to Avalanche (s) | Avalanche Scatter (s) | Max Time to Avalanche (s) | Bulk Density (g/mL) |
|---|---|---|---|---|---|---|
| Control: HPC MXF sieved only | 11.17 | 40 | 12.87 | 5.52 | 21.00 | 0.186 |
| Control: HPC MXF V-Blend w. SiO$_2$ | 12.6 | 51 | 10.08 | 5.74 | 25.33 | 0.211 |
| Invention: Silica coated HPC MXF(DC) | 14.92 | 89 | 5.95 | 3.82 | 17.67 | 0.249 |

Example 8: Flow Characterization Measurement of Polymers by Using Johanson Flow Rate Indicizer All components of the test cell and machine pistons were cleaned. Air connections and air pressure were checked and the air pressure was kept at 25 psi. Weight of the empty test cell was measured and recorded. HPMC K100M sample was fluffed up to break-up lumps and to bring material to minimum bulk density. The sample was loaded and it was distributed evenly by using a spoon. The sample was filled just above the top of the rim. The cell was held at 90° angle and excess material was skimmed off. Weight of the sample with polymer was measured. Similarly measurements for other polymers were also measured. All the measurements of sample were listed in Table 3 (Model Best-Nr: JR FLW; Serial-Nr: FLW 33S)

Example 9: Flow Characterization Measurement of Silica Coated Polymers by Using Johanson Flow Rate Indicizer The same process, which was described in Example 8, was repeated by replacing the polymer sample with silica coated polymer sample. All the measurements of sample were listed in Table 3, 4 and 5.

TABLE 3

Flow and Cohesion characteristics of samples

| Excipient | Processing conditions | | Flow Characterization | Brookfield |
|---|---|---|---|---|
| | RPM (Rotations per minute) | Screen size | (Johanson Flow Rate Index (lb/min) | Cohesion Coefficient (kPa) |
| HPMC K100M | control | | 88 | 0.55 |
| HPMC K100M | 3000 | 0.5 | 269 | 0.166 |

TABLE 3-continued

Flow and Cohesion characteristics of samples

| Excipient | Processing conditions RPM (Rotations per minute) | Screen size | Flow Characterization (Johanson Flow Rate Index (lb/min) | Brookfield Cohesion Coefficient (kPa) |
|---|---|---|---|---|
| DC | | | | |
| HPMC K4M | control | | 234 | 0.27 |
| HPMC K4M DC | 3000 | 0.3 | 462 | 0.127 |
| HPC | control | | 55 | 1.56 |
| HPC DC | 2000 | 0.3 | 106 | 0.92 |
| HEC | control | | 453 | 0.228 |
| HEC DC | 3000 | 0.5 | 534 | 0.027 |
| CMC | control | | 88 | 0.258 |
| CMC DC | 3000 | 0.5 | 146 | 0.024 |

TABLE 4

Cohesion characteristics of samples

| HPMC K100 PH DC | Brookfield Interparticle Cohesion (kPa) |
|---|---|
| Sample 1 | 0.172 |
| Sample 2 (Repeat) | 0.179 |

TABLE 5

Flow and Cohesion characteristics of samples

| Sample/Product | Brookfield Interparticle Cohesion (Pka) | Johanson Flow Rate Index (lb/min) |
|---|---|---|
| HPMC K100 PH DC | 0.408 | 111 |
| HPMC K100 PH DC with Silica on regular blender | 0.272 | 181 |
| HPMC K100 PH DC with Silica as per Example 1 | 0.137 | 260 |
| HPMC K15 | 0.352 | 104 |
| HPMC K15 with Silica on regular blender | 0.304 | 154 |
| HPMC K15 with Silica as per Example 1 | 0.180 | 202 |

Example 10: Pharmaceutical Tablet Preparation

A pharmaceutical tablet was prepared using standard Klucel™ HPC, and Klucel™ HPC DC. The tablet formula was:

TABLE 6

Tablet Composition

| Tablet Composition | | Addition level |
|---|---|---|
| Standard | Invention | (%) |
| Klucel® HPC | Klucel® HPC DC | 50 |
| Theophyline | | 25 |
| Fastflo® Lactose | | 24.5 |
| Magnesium stearate | | 0.5 |
| Total | | 100 |

Figure 1:
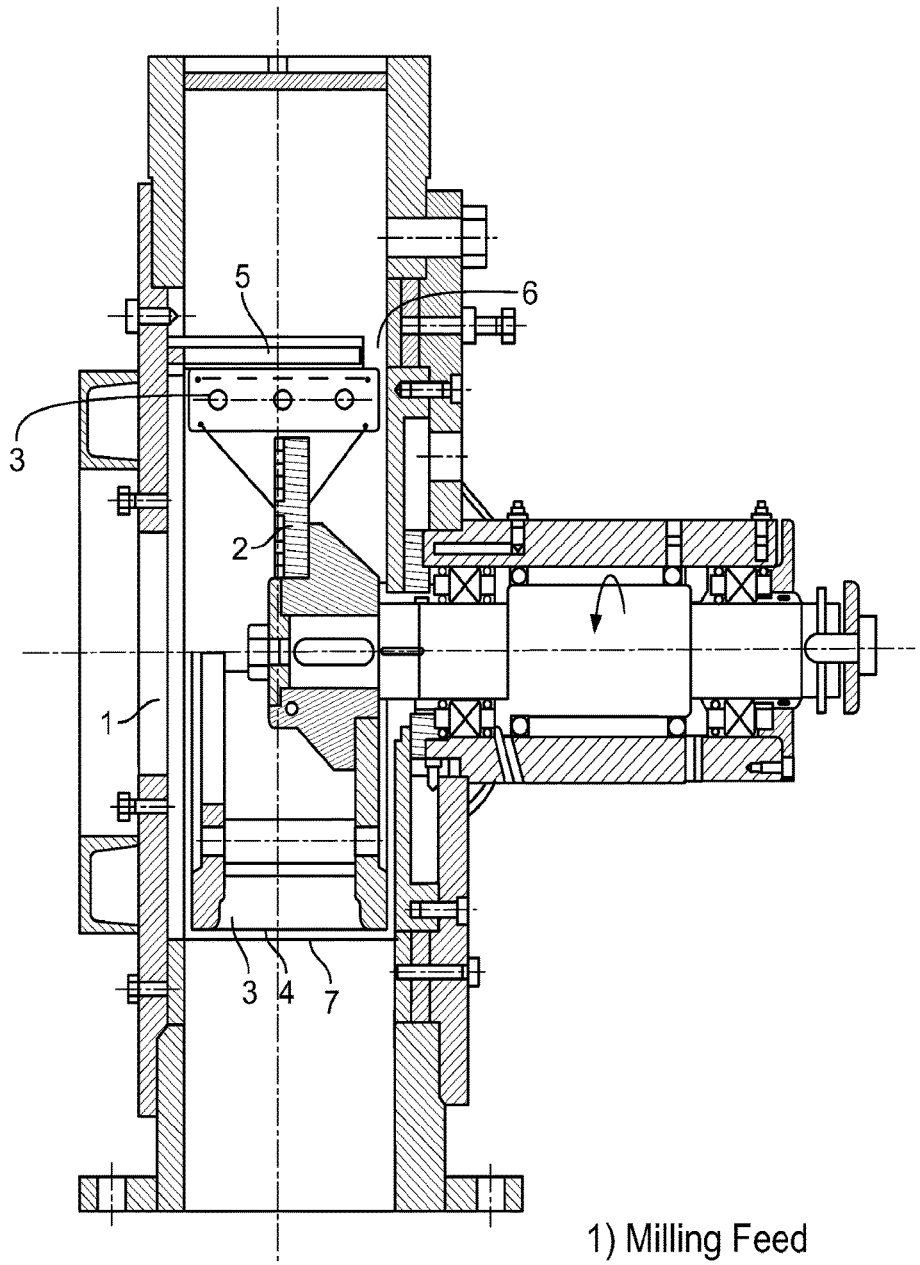
FIG. 1 represents a diagram of a universal mill and its various parts.
Figure 2:
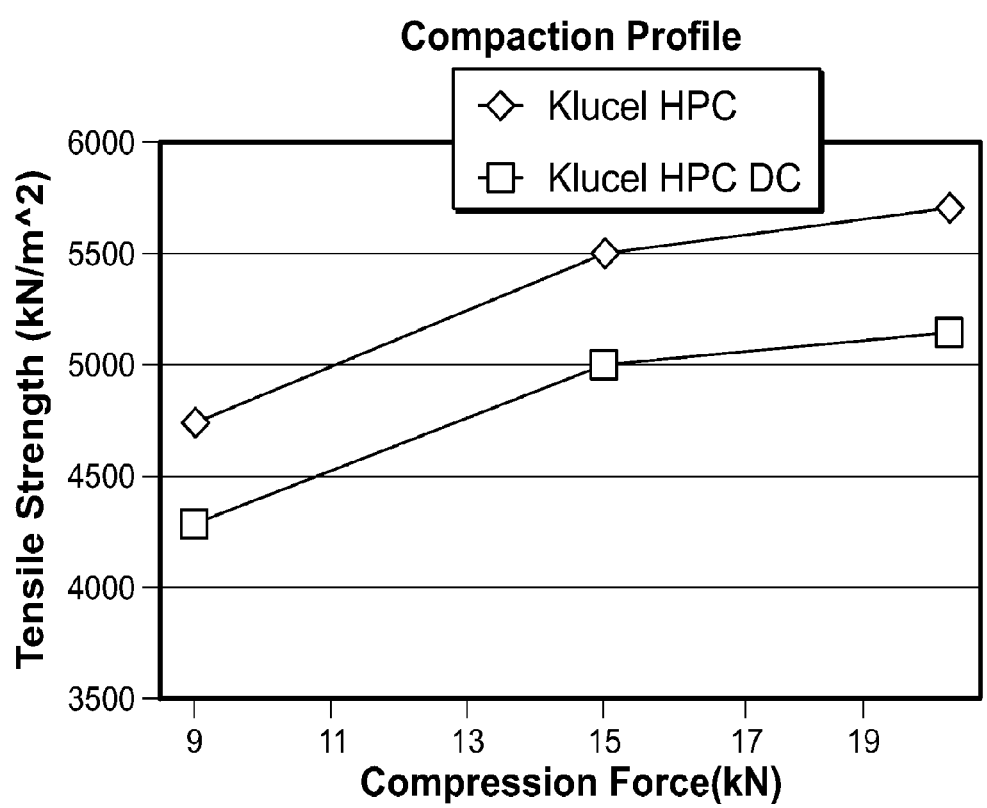
FIG. 2 represents a plot of Tablet Compaction profile.

Hardness of the tablet formulations comprising standard Klucel® HPC, and Klucel® HPC DC were measured and depicted in FIG. 2.

Figure 3:
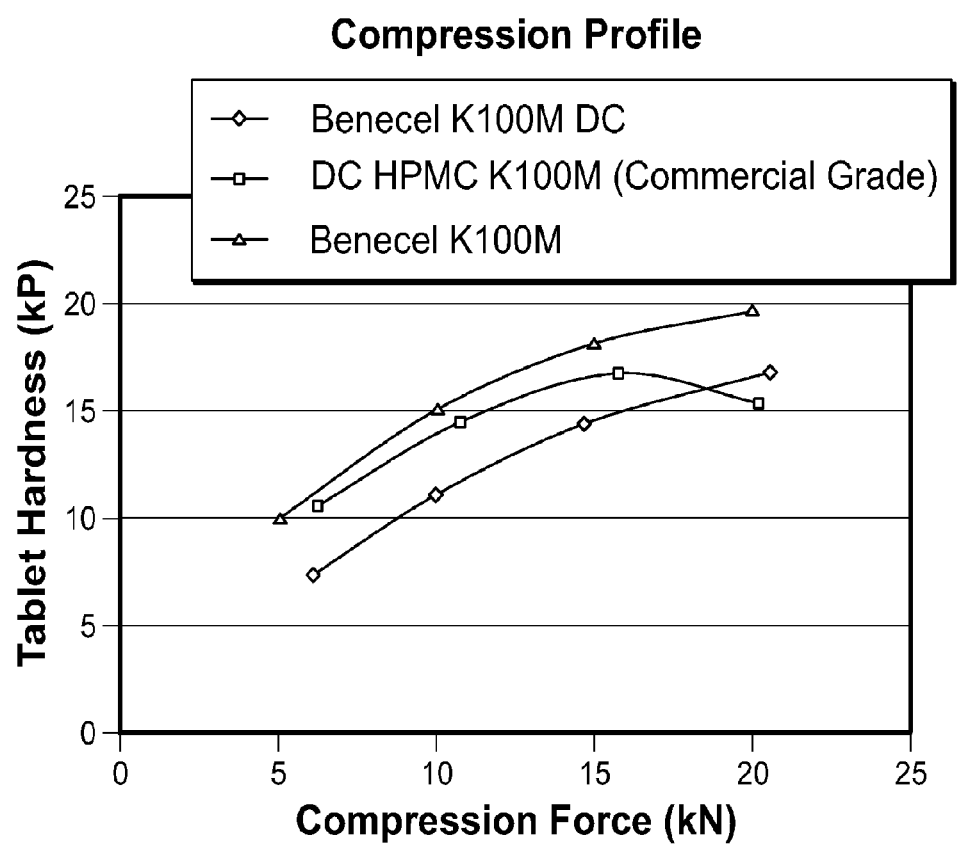
FIG. 3 represents a plot of Tablet Hardness.

Tablet compositions were prepared using HPMC and HPMC DC. Tablet hardness of tablets comprising standard HPMC and HPMC DC grade were measured and depicted in FIG. 3.

Figure 4:
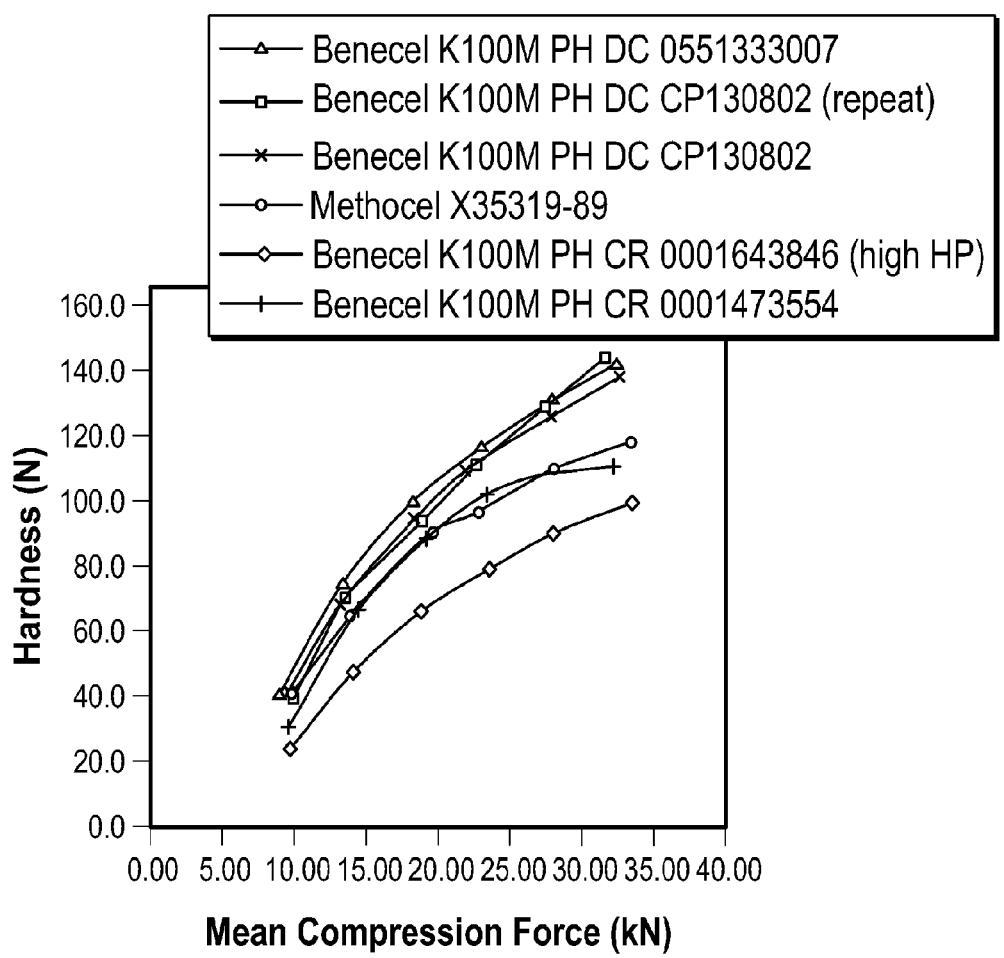
FIG. 4 represents a plot of Compaction profile.
Figure 5:
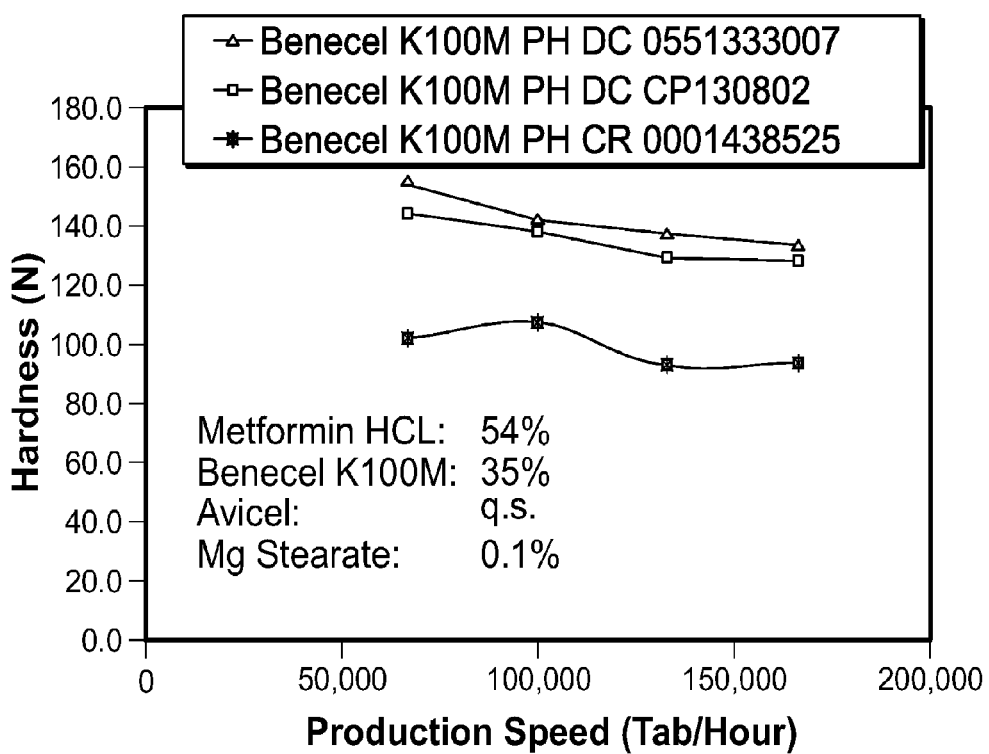
FIG. 5 represents a plot of Metformin Tablet formulation Compaction profile.

Metformin HCL tablet compositions were prepared using standard HPMC CR and HPMC DC. 400 mg tablets were compressed using Stylcam 200R compaction simulator having 11.28 mm flat round Euro D tooling, over a range of 5 KN-25 KN compression force. In-die tablet thickness and corresponding compression force were recorded by the compaction simulator. The tablets were characterized for weight, thickness and hardness after overnight relaxation. Tablet hardness of tablets comprising standard HPMC and HPMC DC grade were measured and depicted in FIG. 4. Impact of scalability on the tablet hardness was studied by increasing the tablet speed from 66,000 tablets/hour to 180,000 tablets/hour as depicted in FIG. 5.

The present invention also provides applications of the coprocessed excipient in paints and coatings, personal care, detergents, pharmaceuticals, neutraceuticals, pet food, animal food, agricultural products, adhesives, electroplating, inks, dyes, paper, catalytic convertors, ceramics, insulators, and electronics.

The invention has been described in detail with particular reference to preferred embodiments thereof, but it will be understood that variations and modifications can be effected within the spirit and scope of the invention.

We claim:

1. A coprocessed excipient comprising:
   (i) about 90.0% w/w to about 99.9% w/w of a cellulose based polymer selected from the group consisting of hydroxyethyl cellulose (HEC), hydroxypropyl cellulose (HPC), hydroxypropyl methylcellulose (HPMC), and carboxymethyl cellulose (CMC); and
   (ii) about 0.1% w/w to about 10.0% w/w of a deagglomerated coprocessing agent selected from the group consisting of fumed silica, colloidal silica, silicon dioxide, and combinations thereof;
   wherein the coprocessed excipient is prepared in a continuous process, where the coprocessing results in silica coating of the cellulose based polymer, and the coprocessed excipient has a Brookfield cohesion of less than 0.20 kPa, a bulk density of at least 0.249 gram/milliliter and a flow property as measured by Johanson flow rate number increase from 1.1 to 5.0 fold.

2. The coprocessed excipient of claim 1, wherein the excipient further optionally comprises a vinyl lactam based polymer selected from the group consisting of N-vinyl-2-pyrrolidone, poly(vinyl pyrrolidone), polyvinyl polypyrrolidone, N-vinyl-2-caprolactam, N-vinyl-3-methyl-2-pyrrolidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam, and combinations thereof.

3. The coprocessed excipient of claim 1, wherein the cellulose based polymer and the coprocessing agent are present in a ratio from about 90:10 to 99.9:0.1.

4. The coprocessed excipient of claim 1, wherein the coprocessed excipient is further combined with an active or functional ingredient selected from the group consisting of a paint, a coating, a personal care ingredient, a detergent, a pharmaceutical, a neutraceutical, a ceramic, an insulator, a pet food animal food, a human food, an agricultural product, an adhesive, an electroplating ingredient, an ink, a dye, a paper ingredient, a catalytic convertor, an electronic, and combinations thereof.

5. A continuous process for preparing a coprocessed excipient according to claim 1 comprising the steps of:
   i. deagglomerating a coprocessing agent using shear in magnitude of at least 0.01 kW-hour/kilogram;
   ii. passing a cellulose based polymer and deagglomerated coprocessing agent through a blender with an average particle residence time of >1 second;
   iii. subjecting the above two components to pass through a universal mill;
   iv. maintaining an average particle residence time within the universal mill system to be >1 second completed by a continuous recycle process; and
   v. obtaining the coprocessed excipient having a Brookfield cohesion of less than 0.20 kPa, a bulk density of at least 0.249 gram/milliliter and improved flow property as measured by Johanson flow rate increased from 1.1 to 5.0 fold.

6. The process of claim 5, wherein the universal mill comprises a rotor with tip speed of about 15 meters/second to about 150 meters/second and screen size of about 0.2 millimeter to about 0.9 millimeter.

7. A composition comprising the coprocessed excipient of claim 1 for use in an industrial application selected from paints and coatings, personal care, detergents, pharmaceuticals, nutraceuticals, ceramics, insulators, pet food, animal food and human food, agricultural products, adhesives, electroplating, inks, dyes, paper, catalytic convertors or electronics.

8. The composition of claim 7, wherein the composition is used in pharmaceuticals.

9. The composition of claim 8, wherein the composition is formulated into an oral dosage form by dry granulation, direct compression, or hot melt extrusion processing.

10. A directly compressible pharmaceutical composition comprising:
   i. an active pharmaceutical ingredient;
   ii. the coprocessed excipient of claim 1; and
   iii. optionally one or more pharmaceutically acceptable additives.

11. The directly compressible pharmaceutical composition of claim 10, wherein the composition is formulated into modified release, controlled release, sustained release, extended release, immediate release or soluble dosage forms.

12. The directly compressible pharmaceutical composition of claim 10, wherein the composition is in the form of a tablet.

13. The process of preparing the directly compressible pharmaceutical composition of claim 10, comprising the steps of:
   i. blending the active pharmaceutical ingredient, the coprocessed excipient of claim 1, and optionally one or more adjuvants; and
   ii. compressing the resulting components to obtain the directly compressible pharmaceutical composition.

* * * * *